United States Patent [19]
Binder et al.

[11] Patent Number: 6,140,337
[45] Date of Patent: Oct. 31, 2000

[54] METHODS FOR THE TREATMENT OF MENTAL DISORDERS

[75] Inventors: Gary Binder, Westfield; Domenic G. Iezzoni, Ridgewood; William Kreutner, West Paterson; Arnold Lash, Branchburg, all of N.J.

[73] Assignee: Schering Corporation, Kenilworth, N.J.

[21] Appl. No.: 09/378,303

[22] Filed: Aug. 20, 1999

Related U.S. Application Data

[63] Continuation-in-part of application No. 09/216,098, Dec. 18, 1998, abandoned
[60] Provisional application No. 60/068,639, Dec. 23, 1997.

[51] Int. Cl.$^7$ .................... A61K 31/435; A61K 31/4545
[52] U.S. Cl. .......................................................... 514/290
[58] Field of Search ............................................ 514/290

[56] References Cited

U.S. PATENT DOCUMENTS

| | | | |
|---|---|---|---|
| 4,659,716 | 4/1987 | Villiani et al. | 514/290 |
| 5,595,997 | 1/1997 | Aberg et al. | 514/290 |
| 5,763,183 | 6/1998 | Pesonen et al. | 435/6 |
| 5,912,335 | 6/1999 | Bergsma et al. | 536/23.5 |

OTHER PUBLICATIONS

Song et al., European Neuropsychopharmacology, 6:157–1162, 1996.
Bell, I.R., et al, "Is Allergic Rhinitis More Frequent in Young Adults With Extreme Shyness? A Preliminary Survey,." Psychosomatic medicine, 52:517–525, 1990.
Kagan, J., et al, "Temperament and Allergic Symptoms", Psychosomatic Medicine, 53:332–340, 1991.
Bell, I.R., et al, "Depression and Allergies : A Survey of a Nonclinical Population," Psychother Psychosom, 55:31, 1991.
Rorsman, B., et al, "Premorbid traits and Psychosomatic Background Factors in Depression : The Lundby study 1957–1972", Neuropsychobiology, 27:72–79, 1993.
Marshall, P.S., "Allergy and Depression : A Neurochemical Threshold Model of the Relation Between the Illnesses," Psychological Bulletin, 113:23–43, 1993.
Gauci, M., et al, "A Minnesota multiphasic Personality Inventory Profile of Women With Allergic Rhinitis," Psychosomatic Medicine, 55:533–540, 1993.
Rao, K.S., et al, "Duration of the Suppressive Effect of Tricyclic Antidepressants on Histamine–induced wheal–and–flare Reactions in Human Skin", J. Allergy Clin Immunol, 82:752–757, 1988.
Wood, K, et al, "Platelet Accumulation of Histamine in Controls, Depressed, and LithiumTreated Patients," J. Affective Disorders, 7:149–158, 1984.
Matussek, P, et al, "Aggression and allergic disorder in depressives", Journal of Psychosomatic Research, 1984; 28:205–211.
Matussek, P., et al, "Allergic Disorders in Depressive Patients," Comprehensive Psychiatry, 24:25–34, 1983.

Sanger, M., "The treatment of Anxiety and Depression in Then Allergic Patient", Annals of Allergy, 27:506–510, 1969.
Leonard, G, "Behavioral manifestations of Allergic Children", Annals of Allergy, 24:248–249, 1966.
Younes, R.P., et al, "Manic–depressive Illness in Children : Treatment with Lithium Carbonate," Journal of Child Neurology, 1:364–368, 1986.
Nasr, S., et al., "Concordance of Atopic and Affective Disorders," Journal of Affective Disorders, 3:291–296, 1981.
Shen et al., "Molecular Cloning and Expression of a 5–Hydroxytryptamine$_7$, Serotonin Receptor Subtype," The Journal of Biological Chemistry, 263:18200–18204, 1993.
Gelernter et al., "Assignment of the 5HT7 Receptor Gene (HTR7) to Chromosome 10q and Exclusion of Genetic Linkage with Tourette Syndrome," Genomics, 26:207–209, 1995.
Thomas et al., "Unique allosteric regulation of 5–hydroxytryptamine receptor–mediated signal transduction by oleamide," Proc. Natl. Acad. Sci. USA, 94:14115–14119, 1997.
Lawler, et al., "Interactions of the Novel Antipsychotic Aripiprazole (OPC–14597) with Dopamine and Serotonin Receptor Subtypes," Neuropsychopharmacology, 20:612–637, 1999.
Rebecca A. Prosser, "Neuropeptide Y blocks serotonergic phase shifts of the suprachiasmatic circadian clock in vitro," Elsevier Brain Research, 808:31–41, 1998.
Jasper et al., "Cloning, expression and pharmacology of a truncated splice variant of the human 5–HT$_7$ receptor (h5–HT$_{7(b)}$," British Journal of Pharmacology, 122:126–132, 1997.
Kennaway et al., "Serotonin agonists mimic the phse shifting effects of light on the melatonin rhythm in rats," Elsevier, Brain Research, 737:301–307, 1996.
Traiffort et al., Interaction of mianserin, amitriptyline and haloperidol with guinea pig cerebral histamine H$_2$ receptors studied with [$^{125}$I] iodoaminopotentidine, European Journal of Pharmacology, 207:143–148, 1991.
Roth et al., "Binding of typical and Atypical Antipsychotic Agents to 5–Hydroxytryptamine–6 and 5–Hydroxytryptamine–7 Receptors," The Journal of Pharmacology and Experimental Therapeutics, 268:1403–1410, 1994.
Wirz–Justice et al., "A Schizophrenic patient with an arrhythmic circadian rest–activity cycle," Elsevier, Psychiatry Research 73:83–90, 1997.
Urbina, et al. "5HT$_{1A}$ Receptor Agonist Differentially Increases Cyclic AMP Concentration in Intact and Lesioned Goldfish Retina. In Vitro Inhibition of Outgrown by Forskolin," Neurochem, Int. 29:453–460, 1996.

(List continued on next page.)

Primary Examiner—Phyllis G. Spivack
Attorney, Agent, or Firm—Donald W. Wyatt

[57] ABSTRACT

The present invention provides methods of treatment of mental disorders comprising administering the anti-allergic medication loratadine or a metabolite thereof to reduce a patient's symptoms of a mental disorder.

34 Claims, No Drawings

OTHER PUBLICATIONS

Pickard et al., "Serotonergic Innervation of the Hypothalamic Suprachiasmatic Nucleus and Photic Regulation of Circadian Rhythms," Biology of the Cell 89:513–523, 1997.

"Guidelines for controlled trials of drugs in migraine," International Headache Society Committee on Clinical Trials in Migraine, Cephalalgia 11, 1991.

Glen D. Solomon, "Therapeutic Advances in Migraine," J. Clin Pharmacol, 33:200–209, 1993.

Kikuchi et al., "Tetrahydrobenzindoles: Selective Antagonists of the 5–$HT_7$ Receptor," Journal of Medicinal Chemistry, 42:533–535, 1999.

Nelson et al., "Cloning and Expression of 5HT7 Receptor from *Xenopus laevis*," Receptors and Channels, 3:61–70, 1995.

David Goldman, "Candidate Genes in Alcoholism," Neuroscience, 3:174–181, 1995.

Peter J. Goadsby, "Serotonin Receptors and the Acute Attack of Migraine," Neuroscience, 5:18–23, 1998.

Dupont et al., "Epinastine WAL 801CL) inhibits the electrical field stimulation–induced cholinergic contractionn in guinea pig and human airways in vitro," European Respiratory Journal 14:1068–1075, 1999.

METHODS FOR THE TREATMENT OF MENTAL DISORDERS

This application is a continuation in part of U.S. patent application Ser. No. 09/216,098 filed Dec. 18, 1998, abandoned which claims the benefit of U.S. provisional application Ser. No. 60/068,639 filed Dec. 23, 1997.

FIELD OF THE INVENTION

The present invention pertains to the treatment of mental or vascular disorders in patients.

BACKGROUND

It has been estimated that approximately 4% of the people in the world suffer from depression, which is not caused by any known underlying neurological disease. Depression affects people in all walks of society, from the very young to the very old. It often occurs without the presence of a precipitating event, and can be unresponsive to psychotherapy, environmental changes or to pharmacotherapy with the currently available medications.

When an individual is suffering from depression, he or she will usually be in a depressed mood, as well as experience a loss of interest or pleasure in all, or almost all, activities. These and associated symptoms last for a period of at least two weeks. The associated symptoms may include, but not be limited to, appetite disturbance, change in weight, sleep disturbance, psychomotor agitation or retardation, decreased energy, feelings of worthlessness or excessive or inappropriate guilt, difficulty thinking or concentrating, and recurrent thoughts of death or suicidal ideation or attempts. Further, a person suffering from depression can also experience fearfulness, anxiety, irritability, brooding or obsessive rumination, excessive concern with physical health, panic attacks, and phobias.

Of those having mental disorders, a correlation between allergic reactions, and particularly rhinitis, to mental disorders, including depression, has been reported. There has as yet, however, been no report of a physiological connection between allergies and mental disorders.

In fact, there does not appear be a direct physiological association between a depressive episode and allergic reactions. For example, while Bell et al. [Psychosom. Med. 52:517 (1990)] describe an interrelation between social anxiety, allergies and distressed affect, such as depression and anxiety, in some persons, the authors conclude that extreme shyness may only be a stable temperamental feature of a person who also has susceptibility to nasal allergies. Likewise, in a separate publication, Bell et al. [Psycother. Psychosom. 55:24 (1991)] report that affective manifestations lack a definitive relation to the duration or severity of allergic disorders.

Other publications reveal further complications in understanding the physiological relationship between allergies and mental disorders. It appears that the susceptibility to mental disorders can extend beyond the allergic sufferers themselves to their relatives. Kagan et al. [Psychosom. Med., 53:332 (1991)] describe temperament disorders in children suffering from hay fever. The authors report that first and second degree relatives of extremely shy children reveal a greater prevalence of hay fever and social anxiety.

Thus, while there are reports of a relationship between allergies and mental disorders, there is no definitive understanding of a physiological connection between these conditions. Without such an understanding, discovery of a method for alleviating mental disorders in those that suffer from them, or reducing the susceptibility of such individuals to mental disorder, can only be done empirically. On the other hand, there are methods for evaluating the functionality of a potential treatment for mental disorders.

Several lines of evidence suggest that an altered activity of brain serotonergic pathways is related to several neuropsychiatric disorders. For example, lower levels of 5-hydroxyindoleacetic (5-HIAA), the main metabolite of serotonin (5-HT) in the cerebrospinal fluid have been reported in clinical studies of aggression, depression, impulsive crime and alcoholism. Several important genes for normal brain serotonin function have been cloned, including tryptophan hydroxylase, the serotonin transporter, monoamine oxidases A and B and several serotonin receptors. In addition, serotonin receptor agonists and antagonists have been developed as drugs for treating specific neuropsychiatric disorders. Drugs with affinity for $5-HT_2$ receptors have been used to treat schizophrenia, Parkinsonism, and anxiety disorders. Several azapirones, such as buspirone, gepirone, and ipsapirone, have high affinities for $5HT_{1A}$ receptors in the brain, and are used to treat anxiety. For example, clozapine which is an antipsychotic drug is used to treat schizophrenic patients who do not respond to other drug treatments. Clozapine has a strong affinity for the serotonin $5-HT_2$ subclass of receptors. In addition, $5-HT_{1A}$ class agonists, such as buspirone, are effective treatments for anxiety. Highly selective 5-HT uptake inhibitors have been used successfully to treat depression.

Much recent interest in serotonin research has concentrated on the $5-HT_7$ receptor. This receptor and allelic variations of it are described in U.S. Pat. No. 5,763,183 as well as Shen et al, *J. Biol. Chem.* 268:18200 and Roth et al, *J. Pharmacol Exp. Ther.* 268:1403.

This receptor is a guanine nucleotide regulatory protein coupled receptor (GPCR) and, on the basis of its sequence, it is thought to have the typical GPCR structure of seven hydrophobic transmembrane helices separated by three extracellular and three intracellular loops. The $5-HT_7$ receptor has a distinct pharmacological profile which includes high affinity for clozapine and related atypical antipsychotic agents as well as for some typical antipsychotic agents.

Pharmacological studies in humans have also suggested that abnormal function of $5-HT_7$ receptors might play a role in the etiology of certain mental/social disorders. These disorders include, but are not limited to, depression, alcoholism, weight management disorders (loss/obesity), social disorder, impotence/sexual dysfunction, panic, obsessive/compulsive disorder. $5-HT_7$ is also present in vascular tissue and can be associated with vascular-associated conditions. These conditions include, but are not limited to, migraines, stroke, orthostatic hypotension, gastrointestinal stasis, nausea, dizziness and jet lag.

Accordingly, a chemical that interacts with this receptor could be a valuable drug.

It is clear that what is needed is a method of treating an at risk population to lessen their risk of mental disorder and depression and vascular diseases. Also needed is a method to treat those that suffer from these disorders to reduce their symptoms of mental disorder.

SUMMARY OF THE INVENTION

The present invention provides methods for treatment of mental and vascular disorders. In one embodiment, the present invention provides a method of treating a patient suffering from mental or vascular disorder, comprising administering an effective amount of an anti-allergic medication to said patient under conditions such that the symptoms of said mental disorder are diminished.

In another embodiment, the present invention provides a method of treating a patient known to have suffered from a mental or vascular disorder, comprising administering an effective amount of an anti-allergic medication to said patient under conditions such that recurrence of the symptoms of said mental disorder are prevented or diminished.

The present invention is not limited to the type of mental disorder. Mental disorders include, but are not limited to, depression, alcoholism, weight management disorders (loss/obesity), social disorder, impotence/sexual dysfunction, panic, obsessive/compulsive disorder. Likewise, the present invention is not limited to the type of vascular disorders. Vascular disorders include, but are not limited to, migraines, stroke, orthostatic hypotension, gastrointestinal stasis, nausea, dizziness and jet lag.

The present invention is not limited to a type of patient having, or having experienced, a mental or vascular disorder. In one embodiment, the patient is susceptible to mental or vascular disorder. Alternatively, the patient may be suffering from a mental or vascular disorder, but not be of a group that is classified as susceptible to a mental or vascular disorder.

Likewise, the present invention is not limited to a specific anti-allergic medication. In one embodiment, the medication is an antihistamine. In a preferred embodiment, the antihistamine is a low-sedating or non-sedating antihistamine. In particularly preferred embodiments, the antihistamine is loratadine or a metabolite of loratadine (e.g., desloratadine).

When an antihistamine is used, it is preferably dosed in a range of 0.001 to 200 milligrams per kilogram. In a further preferred embodiment, the dosage is 0.01 to 100 milligrams per kilogram. In a particularly preferred embodiment, the dosage can be 1.0 to 60 milligrams per kilogram. Alternatively, the dosage is 0.001 to 200 milligrams per day, 0.01 to 100 milligrams per day or 1.0 to 60 milligrams per day.

DETAILED DESCRIPTION OF THE INVENTION

All patents and literature references cited in this specification are hereby incorporated by reference in their entirety.

The present invention contemplates methods of treatment of mental disorders in patients having or being susceptible to a mental disorder. In one embodiment, the present invention contemplates administration of an effective amount of an anti-allergic medication, preferably in a pharmaceutically acceptable carrier or diluent. In another embodiment, a medication commonly used to treat mental disorder is administered in addition to the anti-allergic medication. Alternatively, more than one anti-allergic medication is administered as a combination medication to treat mental disorder. It should be understood that such combination medications can also be further combined with a medication commonly used to treat mental disorder. Such commonly used medications include, but are not limited to, benzodiazepines, monoamine oxidase inhibitors, tetracyclic antidepressants, selective serotonin reuptake inhibitors, tricyclic antidepressants, antipanic agents, antipsychotic agents, phenothiazines, psychostimulants and psychotropics.

As used herein, the term "mental disorder" refers to those provided in the *Diagnostic and Statistical Manual* (*DSM IV*), American Psychological Association (APA). These mental disorders include, but are not limited to affective disorders, neurotic disorders and unspecified depressive disorders. Examples of affective disorders include mood disorders, manic disorder, major depressive disorder and bipolar affective disorder. Mood disorders include, but are not limited to, depressive disorders, dysthymic disorder, bipolar disorders (I and II) and cyclothymic disorders. Likewise, examples of neurotic disorders include, but are not limited to, anxiety states, panic disorders, phobias, obsessive-compulsive disorder, post traumatic stress disorder, acute stress disorder, generalized anxiety disorder, attention deficit hyperactivity disorder, Tourette's Syndrome and hysteria. Other conditions include sleep disorders, including breathing related sleep disorders.

The use of the term "depression" herein is intended to embrace clinical and subclinical forms of depression, particularly endogenous depression whose onset is or does not appear to be brought on by any particular event in the subject human's life.

Thus, the term "depression", as used herein includes those described in DSM IV, including, but not limited to, mood disorders, depression clinically diagnosed by professionals, such as psychiatrists, psychotherapists, psychologists, and therapists, as well as depression which may not be clinically diagnosed by a mental health practitioner but may nevertheless still be severe and prolonged. By way of non-limiting examples, clinically diagnosed depression includes dementia, acute depression, schizophrenia, and other clinical depression disorders, classified in DSM IV.

As used herein, the term "susceptible to mental disorder" and "susceptible to depression" refers to individuals who are at risk for such disorders due to a predisposition to allergic response, such as reactions associated with histamine H1-receptor allergen interactions or abnormal activity associated with the 5-HT$_7$ receptor or by being an immediate relative of someone who suffers such reactions or abnormal activities. Likewise, "susceptible to a vascular disorder" refers to individuals who are at risk for vascular disorders. For example, abnormal activity associated with the 5-HT$_7$ receptor is one, but not the only, way to determine that an individual is susceptible to vascular disorder. Other methods are well known in the art.

As used herein, the term "allergic response" refers to an altered reactivity in response to an antigen and manifesting as various diseases, including, but not limited to, allergic rhinitis (seasonal or perennial, due to pollen or other allergens), asthma, polyps of the nasal cavity, unspecified nasal polyps, pharyngitis, nasopharyngitis, sinusitis, upper respiratory tract hypersensitivity reaction, and other allergies. Examples of allergies include, but are not limited to, allergic rhinitis (seasonal or perennial) or other respiratory allergy, food allergies and atopic skin reactions. Such responses can be Type I that are IgE-mediated immunologic reactions, or they can be Type II that are IgA, IgG or IgM mediated reactions.

As used herein, the term "anti-allergic medication" refers to a medication that controls an allergic response and the associated signs and symptoms of the manifested disease. Examples include, but are not limited to, antihistamines (e.g., histamine H1-receptor and histamine H3-receptor blocking agents), corticosteroids, nasally administered corticosteroids, orally administered corticosteroids, injected corticosteroids, cromones (e.g., cromolyn [Nasalcrom, Rhone-Poulenc Rorer, Collegeville, Pa.]), atopic corticosteroid creams. Examples of corticosteroidal anti-allergic medications include, but are not limited to, beclomethasone

[Beconase AQ and Beconase Inhalation, Glaxo Wellcome, Research Triangle Park, N.C.], dexamethasone [Dexacort Phosphate in Turbinaire, Medeva, Fort Worth, Tex.], fluticasone [Flonase, Glaxo Wellcome, Research Triangle Park, N.C.], triamcinolone [Nasacort AQ and Nasacort, Rhone-Poulenc Rorer, Collegeville, Pa.], flunisolide [Nasalide and Nasarel, Roche, Nutley, N.J.], budesonide [Rhinocort, Astra], beclomethasone [Vancenase AQ, Schering, Madison, N.J.], and mometasone furoate [Nasonex, Schering, Madison, N.J.]. Examples of antihistamines include, but are not limited to, histamine $H_1$-receptor blocking medication, histamine H3-receptor blocking medication, astemizole [Hismanal, Janssen, Titusville, N.J.], azatadine [Trinalin, Schering-Plough Corp., Madison, N.J.], cyproheptadine [Periactin, Merck, Rahway, N.J.], fexofenadine [Allegra, Hoechst Marion Roussel, Kansas City, Mo.], mizolastine, ebastine, loratadine [Claritin, Schering-Plough Corp., Madison, N.J.], desloratadine [also know as descarboethoxyloratadine, see U.S. Pat. Nos. 4,659,716; 5,595,997, and 5,731,319], phenindamine [Nolahist, Hoffman-LaRoche, Nutley, N.J.], terfenadine [Seldane, Hoechst Marion Roussel, Kansas City, Mo.], diphenhydramine [Benadryl, Park Davis, Morris Plains, N.J.], bromodiphenhydramine [Bromo-Benadryl, Park Davis, Morris Plains, N.J.], carbinoxarnine [Rondec, Dura, San Diego, Calif.], clemastine [Tavist, Sandoz, East Hanover, N.J.], dimenhydrinate [dimenhydrinate in Tubex, Wyeth Ayerst, Philadelphia, Pa.], diphenhydramine [Benadryl, Park Davis, Morris Plains, N.J.], diphenylpyraline, doxylamine [Unisom, Pfizer, New York, N.Y.], phenyltoloxarnine [Kutrase, Schwarz, Milwaukee, Wis.], ephedrine [Quadrinale, Knoll, Mount Olive, N.J.], epinephrine, [Epipen, Center, Port Washington, N.Y.], pseudoephedrine, [Claritin-D, Schering, Madison, N.J.], acrivastine [Semprex D, Medeva, Fort Worth, Tex.], brompheniramine [Bromfed, Muro, Tewksbury, Mass.], chlorpheniramine [Children's Tylenol Cold, McNeil, Fort Washington, Pa.], dexbrompheniramine, dexchlorpheniramine, dimethindene, pheniramine [Triarninc, Sandoz, East Hanover, N.J.], pyrrobutamine, triprolidine [Actifed, Warner Wellcome, Morris Plains, N.J.], methdilazine, promethazine [Phenergan, Wyeth-Ayerst, Philadelphia, Pa.], buclizine, cetirizine (Zyrtek, Pfizer, New York, N.Y.], chlorcyclizine [Mantadil, Glaxo Wellcome, Research Triangle Park, N.C.], cyclizine, hydroxyzine [Atarax, Pfizer, New York, N.Y.] and meclizine [Antivert, Pfizer, New York, N.Y.]. Such antihistamines can also be classified as sedating, low-sedating (e.g., cetirizine) or non-sedating (e.g., loratadine).

Dosing amounts and duration may vary according to the individual subject, the severity of the mental disorder or susceptibility to mental disorder and other factors which may affect the pharmaceutical kinetics of drug dosage and delivery. The influence of such factors on drug effectiveness is well-recognized in the art.

The compositions of the present invention may be administered in a number of pharmaceutically acceptable formulations including, for example, tablets and caplets. Preferably, the compositions are administered orally for ease of convenience.

Liquid formulations (oral or parenteral) are also contemplated. In addition, the compositions may take the form of suppositories, suitable for rectal administration. Those skilled in the art will appreciate that the forms of the compositions and amounts of the anti-allergic medication therein, may vary within pharmaceutically acceptable limits and still embrace the concept of this invention.

While the present invention is not limited to treatment in direct response to a mental disorder, in one embodiment the anti-allergic medication is administered in response to symptoms of a mental disorder. For example, a patient diagnosed with depression may be treated to relieve the symptoms of depression. Alternatively, a patient known to have suffered from a mental disorder may be given an anti-allergic medication to prevent a recurrence or to lessen the severity of the symptoms of a mental disorder, even though no symptoms are evident at the time of administration.

Likewise, the present invention is not limited to the type of patient suffering from or susceptible to a mental disorder. In one embodiment, the patient suffers from a mental disorder with no known physical disorder. On the other hand, the patient may suffer from a mental disorder and also be subject to allergic reactions, including allergic responses. For example, a patient subject to a mental disorder may also suffer periodic bouts of hay fever. In such a case, the present invention contemplates treatment of the mental disorder with an anti-allergic medication.

While not limited to any particular anti-allergic medications, the present invention contemplates administration of antihistamines to patients having symptoms of a mental disorder. In a preferred embodiment, the mental disorder is depression. Likewise, in such preferred embodiments, the antihistamines can be low-sedating or non-sedating antihistamines.

EXAMPLE 1

Identification of Correlation Between Mental Disorders and Allergic Responses

In this example, the correlation of mental disorder to an allergic response (e.g., allergic respiratory disorders) is investigated. The medical records of 350,000 patients over two years were reviewed for correlation between their physical ailments and mental health claims. Of the allergic response claims reviewed, the correlation between those that suffer from allergic response to mental health claims was high. Mood disorders and anxiety disorders were of the most statistically correlated affective disorders associated with allergic response. The following table summarize the results.

TABLE 1

| | Confidence Intervals for Ratios of (% of Non-Allergy) to (% of Allergy) | | | | | | | | |
|---|---|---|---|---|---|---|---|---|---|
| | # of Patients | | % of | % of | | Confidence Intervals | | | |
| Disorder | Non-Allergy | Allergy | Non-Allergy | Allergy | Ratio | 95% | | 99% | |
| Mood Disorders | 3204 | 1161 | 1.14 | 2.03 | 1.79 | 1.67 | 1.91 | 1.64 | 1.95 |
| Anxiety Disorders | 7530 | 2591 | 2.61 | 4.53 | 1.74 | 1.66 | 1.82 | 1.64 | 1.84 |
| Unspecified Depressive Disorders | 2780 | 959 | 0.99 | 1.68 | 1.70 | 1.58 | 1.83 | 1.55 | 1.87 |

These confidence levels are derived from confidence intervals on the log(odds ratio). The log(odds ratio) confidence intervals are based upon a large sample normal approximation and the delta method. To calculate intervals with different confidence levels, use the equation:

$$R = (p_1/p_2)$$

$$S_{\text{Log}R}[(1-p_1)/p_1 n_1 + (1-p_2)/p_2 n_2]^{1/2}$$

$$LCL = \exp(\log R - Z_{a/2} S_{\log R})$$

$$UCL = \exp(\log R + Z_{a/2} S_{\log R})$$

For hypothesis testing, the hypothesis that the ratio p1/p2=1 is the same as the hypothesis that the difference p1−p2=0. The latter form of the hypothesis is easily tested using standard test for the difference of two binomial populations. The resulting p-values are:

TABLE 2

| | p-values | |
|---|---|---|
| Disorder | | p-value |
| Mood Disorders | 1.58e-066 | p < 0.001 |
| Anxiety Disorders | 4.63e-133 | p < 0.001 |
| Unspecified Depressive | 4.68e-047 | p < 0.001 |

The confidence intervals are a measure of the statistical significance of a hypothesis when tested. The benefit of the p-value is that it can be used to determine if a value is statistically significant even in a small sample. In the data set forth above, the confidence levels for all three mental health categories in their relationship to allergies were less than 0.001. In that the lower the p-value the greater the confidence level, these data represent a very high confidence level and correlation of allergic inflammation to mental disorder.

EXAMPLE 2

Administration of Low-sedating or Non-sedating Antihistamines to Relieve Mental Disorder Patients suffering from clinical depression are administered a non-sedating antihistamine (loratadine) or a low-sedating antihistamine (cetirizine) to relieve the symptoms of depression. Six treatment groups are contemplated.

In Group I, patients suffering from depression are administered loratadine to relieve the symptoms of depression. A significant number of patients experience a reduction of their symptoms of depression. For those still suffering from the symptoms of depression after 14 days, the dosage of loratadine is increased. A significant number of these patients experience a reduction of their symptoms of depression.

In a Group II, patients from Group I whose symptoms of depression were reduced or completely relieved continue treatment with loratadine at their respective dosage level. Of these patients, a significant number of patients do not experience recurrence or worsening of symptoms of depression. Of those patients that do experience recurrence or worsening of symptoms of depression, an increase in the dosage of loratadine reduces these symptoms.

In Group III, patients known to have suffered from depression, but not currently experiencing symptoms of depression, are administered loratadine indefinitely. Of these patients, a significant number of patients do not experience recurrence of symptoms of depression. Of those patients that do experience recurrence of symptoms of depression, an increase in the dosage of loratadine reduces these symptoms.

In Group III, patients suffering from depression are administered cetirizine to relieve the symptoms of depression. A significant number of patients experience a reduction of their symptoms of depression. For those still suffering from the symptoms of depression after 14 days, the dosage of cetirizine is increased. A significant number of these patients experience a reduction of their symptoms of depression.

In a Group V, patients from Group IV whose symptoms of depression were reduced or completely relieved continue treatment with cetirizine at their respective dosage level. Of these patients, a significant number of patients do not experience recurrence or worsening of symptoms of depression. Of those patients that do experience recurrence or worsening of symptoms of depression, an increase in the dosage of cetirizine reduces these symptoms.

In Group VI, patients known to have suffered from depression, but not currently experiencing symptoms of depression, are administered cetirizine indefinitely. Of these patients, a significant number of patients do not experience recurrence of symptoms of depression. Of those patients that do experience recurrence of symptoms of depression, an increase in the dosage of cetirizine reduces these symptoms.

EXAMPLE 3

Administration Of Non-sedating Antihistamine Or Low-sedating Antihistamine To Relieve Mental Disorder In Patients Subject To Allergic Response Patients that suffer from clinical depression and allergic rhinitis are administered a non-sedating antihistamine (loratadine) or a low-sedating antihistamine (cetirizine) to relieve the symptoms of depression. Twelve treatment groups are contemplated.

In Group I, patients suffering from depression and subject to allergic rhinitis, but not currently suffering symptoms of allergic rhinitis, are administered loratadine to relieve the symptoms of depression. A significant number of patients experience a reduction of their symptoms of depression. For those still suffering from the symptoms of depression after 14 days, the dosage of loratadine is increased. A significant number of these patients experience a reduction of their symptoms of depression.

In a Group II, patients from Group I whose symptoms of depression were reduced or completely relieved continue treatment with loratadine at their respective dosage level. Of these patients, a significant number of patients do not experience recurrence or worsening of symptoms of depression. Of those patients that do experience recurrence or worsening of symptoms of depression, an increase in the dosage of loratadine reduces these symptoms.

In Group III, patients known to have suffered from depression and subject to allergic rhinitis, but not currently experiencing symptoms of depression or allergic rhinitis, are administered loratadine indefinitely. Of these patients, a significant number of patients do not experience recurrence of symptoms of depression. Of those patients that do experience recurrence of symptoms of depression, an increase in the dosage of loratadine reduces these symptoms.

In Group IV, patients suffering from depression and subject to allergic rhinitis, but not currently suffering from allergic rhinitis, are administered cetirizine to relieve the symptoms of depression. A significant number of patients experience a reduction of their symptoms of depression. For those still suffering from the symptoms of depression after 14 days, the dosage of cetirizine is increased. A significant number of these patients experience a reduction of their symptoms of depression.

In a Group V, patients from Group IV whose symptoms of depression were reduced or completely relieved continue treatment with cetirizine at their respective dosage level. Of these patients, a significant number of patients do not experience recurrence or worsening of symptoms of depression. Of those patients that do experience recurrence or worsening of symptoms of depression, an increase in the dosage of cetirizine reduces these symptoms.

In Group VI, patients known to have suffered from depression and subject to allergic rhinitis, but not currently experiencing symptoms of depression or allergic rhinitis, are administered cetirizine indefinitely. Of these patients, a significant number of patients do not experience recurrence of symptoms of depression. Of those patients that do experience recurrence of symptoms of depression, an increase in the dosage of cetirizine reduces these symptoms.

In Group VII, patients suffering from depression and allergic rhinitis are administered loratadine to relieve the symptoms of depression. A significant number of patients experience a reduction of their symptoms of depression. For those still suffering from the symptoms of depression after 14 days, the dosage of loratadine is increased. A significant number of these patients experience a reduction of their symptoms of depression.

In a Group VIII, patients from Group VII whose symptoms of depression were reduced or completely relieved continue treatment with loratadine at their respective dosage level. Of these patients, a significant number of patients do not experience recurrence or worsening of symptoms of depression. Of those patients that do experience recurrence or worsening of symptoms of depression, an increase in the dosage of loratadine reduces these symptoms.

In Group IX, patients known to have suffered from depression and suffering from allergic rhinitis, but not currently experiencing symptoms of depression, are administered loratadine indefinitely. Of these patients, a significant number of patients do not experience recurrence of symptoms of depression. Of those patients that do experience recurrence of symptoms of depression, an increase in the dosage of loratadine reduces these symptoms.

In Group X, patients suffering from depression and allergic rhinitis, are administered cetirizine to relieve the symptoms of depression. A significant number of patients experience a reduction of their symptoms of depression. For hose still suffering from the symptoms of depression after 14 days, the dosage of cetirizine is increased. A significant number of these patients experience a reduction of their symptoms of depression.

In a Group XI, patients from Group X whose symptoms of depression were reduced or completely relieved continue treatment with cetirizine at their respective dosage level. Of these patients, a significant number of patients do not experience recurrence or worsening of symptoms of depression. Of those patients that do experience recurrence or worsening of symptoms of depression, an increase in the dosage of cetirizine reduces these symptoms.

In Group XI, patients known to have suffered from depression and suffering from allergic rhinitis, but not currently experiencing symptoms of depression, are administered cetirizine indefinitely. Of these patients, a significant number of patients do not experience recurrence of symptoms of depression. Of those patients that do experience recurrence of symptoms of depression, an increase in the dosage of cetirizine reduces these symptoms.

EXAMPLE 4

Evaluation of Desloratadine Interaction With The 5-HT$_7$ Receptor

Desloratadine, a metabolite of loratadine, was evaluated for its interaction with the 5-HT$_7$ receptor in enzyme assays, radioligand binding assays and cellular assays.

A radioligand binding assay was used to evaluate the interaction of drugs with the serotonin 5HT$_7$ receptor. The assays were conducted as described in the publications by Shen et. al. (J. Biol. Chem. 268, 18200–18204, 1993) and by Rothet. al. (J. Pharmacol. Exp. Ther. 268, 1403–1410, 1993). Briefly, the test compound was dissolved in a solvent of DMSO and added to sample vials which contained a human recombinant 5HT7 receptor and 3H-LSD as the labeled ligand for the 5HT7 receptor. The samples were incubated at 37° C. for 120 min to reach equilibrium.

In separate vials nonspecific binding was determined with the addition of 5 $\mu$M of serotonin. Specific binding was determined to be 90%. The ability of test compounds to displace 3H-LSD from binding to the 5HT7 receptor was measured and potency is expressed as an inhibition constant (Ki) calculated as described by Cheng and Prusoff (Biochem. Pharmacol. 22, 3099–3108, 1973).

Using this assay, desloratadine was found to exhibit a potent interaction with the 5HT7 receptor. The Ki was 204 nM. Therefore, it can be expected that desloratadine can interact appreciably with the 5HT7 receptor to exert beneficial effects in the etiology of certain disorders which include depression, alcoholism and other mental disorders.

From the above, it is clear that the present invention provides a method of treating a population at risk of mental or vascular disorder to lessen their risk of mental disorders or vascular disorders. Also provided is a method to treat those that suffer from a mental or vascular disorder to reduce their symptoms of the mental or vascular disorder.

We claim:

1. A method for treating a patient suffering from a mental disorder, comprising administering loratadine or a metabolite of loratadine to said patient, wherein said mental disorder is selected from the group consisting of depression, alcoholism, weight management disorders, social disorder, impotence/sexual dysfunction, panic and obsessive/compulsive disorder.

2. The method of claim 1, wherein said anti-allergic medication is loratadine.

3. The method of claim 2, wherein said loratadine is provided to said patient in a dosage comprising 0.001 to 200 milligrams per kilogram per day.

4. The method of claim 3, wherein said loratadine is provided to said patient in a dosage comprising 0.01 to 100 milligrams per kilogram per day.

5. The method of claim 4, wherein said loratadine is provided to said patient in a dosage comprising 1.0 to 60 milligrams per kilogram per day.

6. The method of claim 1, wherein said anti-allergic medication is a metabolite of loratadine.

7. The method of claim 6, wherein said metabolite of loratadine is desloratadine.

8. The method of claim 7, wherein said desloratadine is provided to said patient in a dosage comprising 0.001 to 200 milligrams per kilogram per day.

9. The method of claim 8, wherein said desloratadine is provided to said patient in a dosage comprising 0.01 to 100 milligrams per kilogram per day.

10. The method of claim 9, wherein said desloratadine is provided to said patient in a dosage comprising 1.0 to 60 milligrams per kilogram per day.

11. A method for treating a patient suffering from a mental disorder, comprising administering a medication comprising an effective amount of an anti-allergic medication, comprising loratadine or metabolite of loratadine, to said patient to diminish the symptoms of said mental disorder, wherein said mental disorder is selected from the group consisting of depression, alcoholism, weight management disorders, social disorder, impotence/sexual dysfunction, panic and obsessive/compulsive disorder.

12. The method of claim 11, wherein said anti-allergic medication is loratadine.

13. The method of claim 12, wherein said mental disorder is depression.

14. The method of claim 13, wherein said loratadine is provided to said patient in a dosage comprising 0.001 to 200 milligrams per kilogram per day.

15. The method of claim 14, wherein said loratadine is provided to said patient in a dosage comprising 0.01 to 100 milligrams per kilogram per day.

16. The method of claim 15, wherein said loratadine is provided to said patient in a dosage comprising 1.0 to 60 milligrams per kilogram per day.

17. The method of claim 11, wherein said anti-allergic medication is a metabolite of loratadine.

18. The method of claim 17, wherein said metabolite of loratadine is desloratadine.

19. The method of claim 18, wherein said mental disorder is depression.

20. The method of claim 19, wherein said desloratadine is provided to said patient in a dosage comprising 0.001 to 200 milligrams per kilogram per day.

21. The method of claim 20, wherein said desloratadine is provided to said patient in a dosage comprising 0.01 to 100 milligrams per kilogram per day.

22. The method of claim 21, wherein said desloratadine is provided to said patient in a dosage comprising 1.0 to 60 milligrams per kilogram per day.

23. A method for treating a patient susceptible to a mental disorder, comprising administering a medication comprising an effective amount of an anti-allergic medication, comprising loratadine or metabolite of loratadine, to said patient to diminish the symptoms of said mental disorder, wherein said mental disorder is selected from the group consisting of depression, alcoholism, weight management disorders, social disorder, impotence/sexual dysfunction, panic and obsessive/compulsive disorder.

24. The method of claim 23, wherein said anti-allergic medication is loratadine.

25. The method of claim 24, wherein said mental disorder is depression.

26. The method of claim 25, wherein said loratadine is provided to said patient in a dosage comprising 0.001 to 200 milligrams per kilogram per day.

27. The method of claim 26 wherein said loratadine is provided to said patient in a dosage comprising 0.01 to 100 milligrams per kilogram per day.

28. The method of claim 27, wherein said loratadine is provided to said patient in a dosage comprising 1.0 to 60 milligrams per kilogram per day.

29. The method of claim 23, wherein said anti-allergic medication is a metabolite of loratadine.

30. The method of claim 29, wherein said metabolite of loratadine is desloratadine.

31. The method of claim 30, wherein said mental disorder is depression.

32. The method of claim 31, wherein said desloratadine is provided to said patient in a dosage comprising 0.001 to 200 milligrams per kilogram per day.

33. The method of claim 32, wherein said desloratadine is provided to said patient in a dosage comprising 0.01 to 100 milligrams per kilogram per day.

34. The method of claim 33, wherein said desloratadine is provided to said patient in a dosage comprising 1.0 to 60 milligrams per kilogram per day.

* * * * *